(12) United States Patent
Chappuis

(10) Patent No.: US 8,216,133 B2
(45) Date of Patent: Jul. 10, 2012

(54) DOPPLER RETRACTOR

(76) Inventor: James L. Chappuis, Marietta, GA (US)

( * ) Notice: Subject to any disclaimer, the term of this patent is extended or adjusted under 35 U.S.C. 154(b) by 1038 days.

(21) Appl. No.: 11/712,277

(22) Filed: Feb. 28, 2007

(65) Prior Publication Data

US 2007/0276188 A1 Nov. 29, 2007

Related U.S. Application Data

(60) Provisional application No. 60/802,655, filed on May 23, 2006.

(51) Int. Cl.
*A61B 5/02* (2006.01)

(52) U.S. Cl. .................................... 600/202

(58) Field of Classification Search ........... 600/201–246
See application file for complete search history.

(56) References Cited

U.S. PATENT DOCUMENTS

| | | | |
|---|---|---|---|
| 4,945,896 A * | 8/1990 | Gade | 600/202 |
| 5,769,781 A * | 6/1998 | Chappuis | 600/202 |
| 6,795,732 B2 * | 9/2004 | Stadler et al. | 607/17 |
| 7,229,465 B2 * | 6/2007 | Burbank et al. | 606/205 |
| 2002/0177753 A1 * | 11/2002 | Dobrovolny | 600/234 |
| 2002/0193666 A1 * | 12/2002 | Sherts et al. | 600/231 |
| 2005/0119531 A1 * | 6/2005 | Sharratt | 600/227 |
| 2006/0058674 A1 * | 3/2006 | Olstad | 600/450 |
| 2006/0206009 A1 * | 9/2006 | Von Wald et al. | 600/231 |
| 2007/0213597 A1 * | 9/2007 | Wooster | 600/234 |

* cited by examiner

*Primary Examiner* — Eduardo C Robert
*Assistant Examiner* — Tara Carter
(74) *Attorney, Agent, or Firm* — McHale & Slavin, P.A.

(57) ABSTRACT

A surgical retractor comprises an arm having a first end and a second end. A blade has an outer surface and a contact surface. The blade is fixed to at least one of the first end and the second end of the arm. A transducer is disposed on the contact surface of the blade. A Doppler ultrasound sensor is in electrical communication with the transducer. The transducer transmits signals to the Doppler ultrasound sensor that can be used to calculate blood flow rate proximate to a surgical site where the surgical retractor is being used.

17 Claims, 3 Drawing Sheets

DOPPLER RETRACTOR

CROSS REFERENCE TO RELATED APPLICATION

This application is a utility application that claims the benefit of and priority to U.S. Provisional Application Ser. No. 60/802,655, filed on May 23, 2006, which is incorporated by reference herein.

TECHNICAL FIELD

The present invention is generally related to surgical equipment.

BACKGROUND

A retractor is an instrument used during surgery for drawing back and holding in position the edges of a surgical site. The opening created at the surgical site is maintained in a certain manner to provide at least surgical access and in some cases may be used to provide visual access as well. In use, retractors often put pressure on blood vessels. In some applications of retractors, such as, for example, surgery on the lower back, the retractor applies pressure to major blood vessels that supply blood to the pelvis and legs.

The human spine is composed of a column of thirty-three bones, called vertebrae, and the joining structures. The twenty-four vertebrae nearest the head are separate bones and are capable of individual movement. These vertebrae are generally connected by anterior and posterior longitudinal ligaments and by discs of fibrocartilage, called intervertebral discs, positioned between opposing faces of adjacent vertebral bodies. The remaining nine vertebrae are fused to form the sacrum and the coccyx and are incapable of individual movement. The vertebral body and the dorsal vertebrae enclose an opening termed the vertebral foramen, through which the spinal cord, a column of nerve tissue which communicates nerve impulses between the brain and the rest of the body, and spinal nerve roots pass and are protected from damage.

The intervertebral discs are sometimes damaged by local pressure on the spinal cord or excessive bending of the spinal cord which can result in disorders associated with blockage of the nerve impulses traveling along the spinal cord, in turn producing pain, paresthesia, or loss of motor control which must be resolved by removing the causative condition. Also, herniation of the intervertebral disc can occur, in which a small amount of tissue protrudes from the sides of the disc into the foramen to compress the spinal cord. Another common condition involves the development of small bone spurs, called osteophytes along the posterior surface of the vertebral body, again impinging on the spinal cord.

Surgery is often required to correct the above and other problems. In one procedure, the involved vertebral bodies are exposed and the intervertebral disc is removed or replaced. When such a surgery is performed toward the lower portion of the spine major, blood vessels that supply blood to the legs and pelvis often need to be held out of the surgical site with retractors in order to perform the surgery. Excessive retraction of those major blood vessels can result in compromised blood flow to the pelvis and legs. Currently, direct palpation of pulse distal to the retractor is the only indication of excessive retraction.

SUMMARY OF THE INVENTION

Surgical retractors are provided. Briefly described, an exemplary embodiment of a surgical retractor comprises an arm, having a first end and a second end, and a blade having an outer surface and a contact surface. The blade is fixed to at least one of the first end and the second end of the arm. A transducer is disposed on the contact surface of the blade. A Doppler ultrasound sensor is in electrical communication with the transducer. The transducer transmits signals to the Doppler ultrasound sensor that can be used to calculate blood flow rate proximate to a surgical site where the surgical retractor is being used.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

Figure 1:
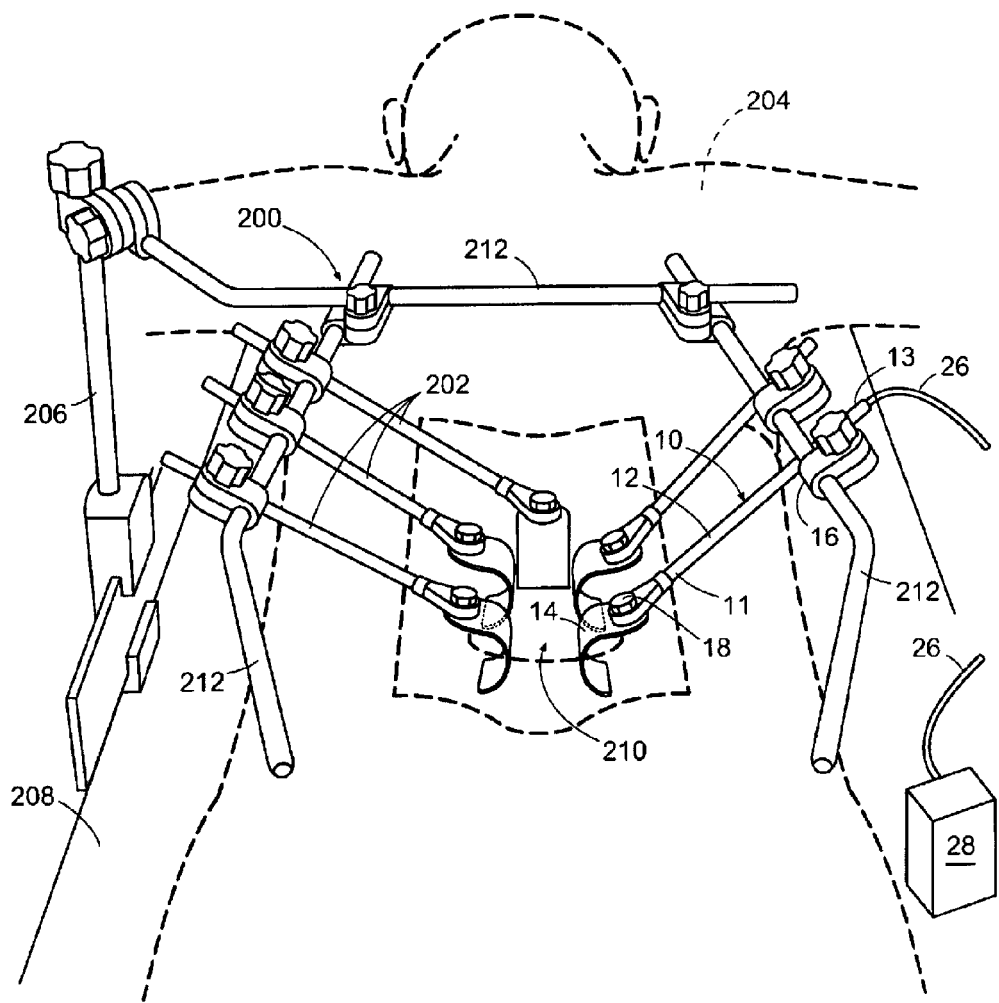
FIG. 1 illustrates an embodiment of a Doppler retractor fixed to a retractor frame.

FIG. 1 illustrates one preferred embodiment of Doppler retractor 10 of the present invention in use. In this embodiment, Doppler retractor 10 is removably and adjustably fixed to retractor frame 200.

Retractor frame 200, as known to those having ordinary skill in the art, is used to set and maintain the desired position of at least one retractor 202 during a surgical procedure. The retractor 202 is used to hold open a surgical site 210 to provide surgical access and even visual access into patient 204. Retractor frame 200 comprises a plurality of bar supports 212 arranged and configured to be suspended over patient 204. Frame 200 is held in position by frame support arm 206. Frame support arm 206 is fixed to table 208 on which patient 204 is positioned for the surgical procedure. Retractors 202 are fixed to support bar 212 and thereby maintained in a desired position over surgical site 210.

Doppler retractor 10 includes arm 12 and blade 14. Arm 12 is substantially elongated and defined by first end 11 and second end 13. Arm 12 can be fixed to support bar 212 of retractor frame 200 with connector 16. Connector 16 is preferably movably positioned on support bar 212 of frame 200. Connector 16 preferably movably receives arm 12 of Doppler retractor 10.

Arm 12 supports blade 14 on one of first end 11 and second end 13, such that blade 14 opposes support bar 212 of frame 200 to which arm 12 is fixed. Blade 14 can be fixed to arm 12 with blade connector 18. Blade connector 18 preferably allows for loosening and tightening of the fixation between blade 14 and arm 12. In this manner, blade 14 can be positioned as desired with respect to arm 12 and then tightened to maintain that desired position.

Doppler ultrasound sensor 28 is also included. Doppler ultrasound sensor 28 is similar to any ultrasound sensor. As one example, Doppler ultrasound sensor 28 may include a central processing unit (CPU), transducer pulse controls and a display, such as an LCD display. Doppler ultrasound sensor 28 may also include additional equipment, such as a printer, disk storage, and a computer monitor such as a cathode ray tube (CRT) monitor.

Figure 2:
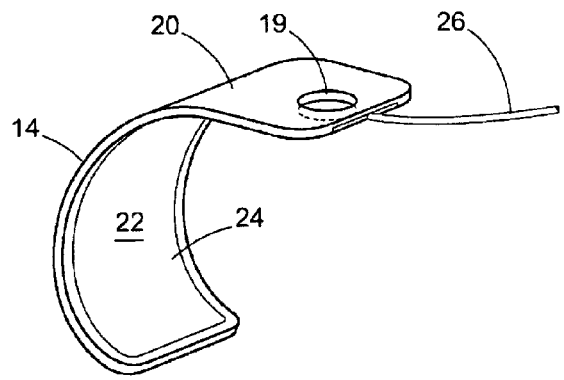
FIG. 2 illustrates the blade of the Doppler retractor of FIG. 1.

Doppler ultrasound sensor 28 may also include a blood flow rate indicator, which could be presented visually, for example, with a light indicator such as an LED, or audibly, for example, with a speaker, both adapted to indicate when a preset blood flow rate has been achieved. Doppler ultrasound sensor 28 may also include an audible sensor adapted to indicate when a preset blood flow rate has been achieved, or to indicate the sound of blood flow. Doppler ultrasound sensor 28, in several embodiments, may be used to calculate blood flow rate proximate to a surgical site where the surgical retractor is being used FIG. 2 illustrates an embodiment of blade 14 in greater detail. As illustrated, blade 14 is curved. It should be understood that blade 14 can have any suitable configuration such that it holds arm 12 in place. Blade 14 comprises outer surface 20 and contact surface 22. Contact surface 22 contacts patient 204 at surgical site 210 to maintain surgical site 210 in the desired open position. Transducer 24 is located adjacent to contact surface 22. Transducer 24 may include, as a non-limiting example, a piezo-electric crystal. Blade 14 further comprises blade connector aperture 19. Blade connector aperture 19 is arranged and configured to receive a portion of blade connector 18 in order to attach blade 14 to arm 12. It should be noted that although blade connector aperture 19 is illustrated as being substantially circular, blade connector aperture 19 is not limited to a circular shape. Wire 26 extends from transducer 24 to Doppler ultrasound sensor 28. Wire 26 facilitates electronic communication between transducer 24 and Doppler ultrasound sensor 28.

Figure 3:
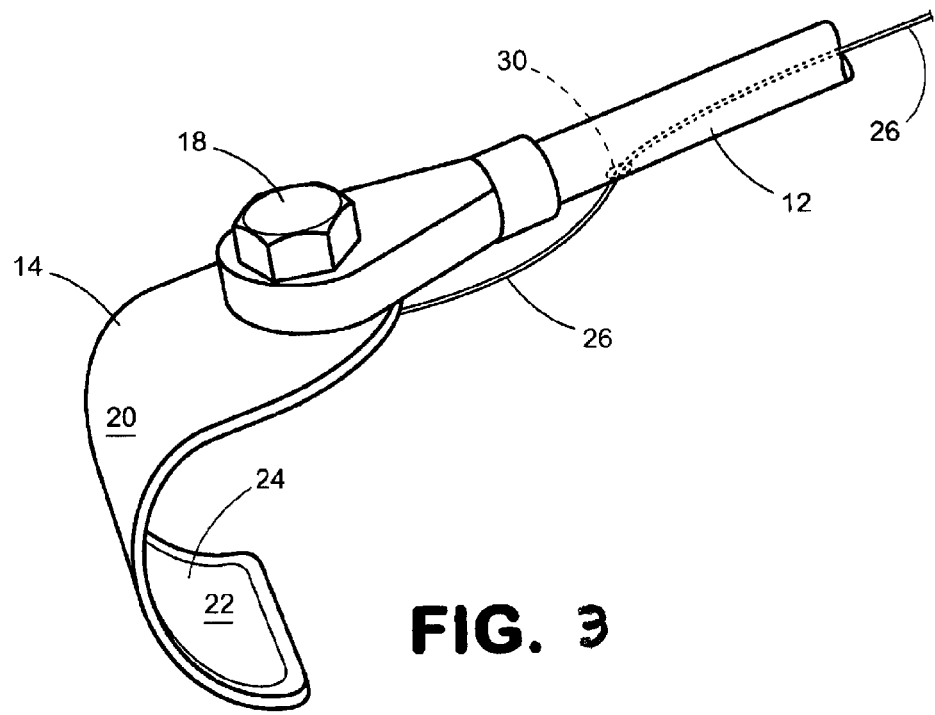
FIG. 3 illustrates the blade and the arm of the Doppler retractor of FIG. 1.

FIG. 3 illustrates blade 14 fixed to arm 12 with blade connector 18. Blade 14 may be configured as disclosed above. Arm 12 includes aperture 30 and a hollow cavity within arm 12. Wire 26 that extends from transducer 24 enters the hollow cavity of arm 12 through aperture 30.

Figure 4:
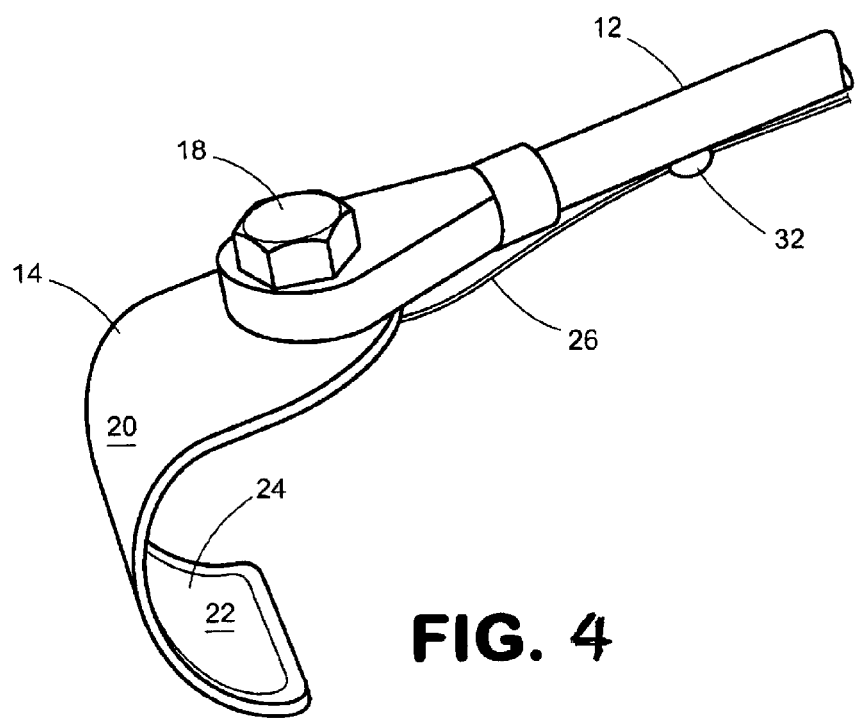
FIG. 4 illustrates the blade and the arm of the Doppler retractor FIG. 1.

FIG. 4 illustrates blade 14 fixed to arm 12 with blade connector 18. Blade 14 may be configured as disclosed above. Arm 12 includes clips 32 located along the length of arm 12. Clips 32 releasably grip wire 26 that extends from transducer 24 to Doppler ultrasound sensor 28. Clip 32 may maintain wire 26 substantially adjacent to arm 12 during use.

Figure 5:
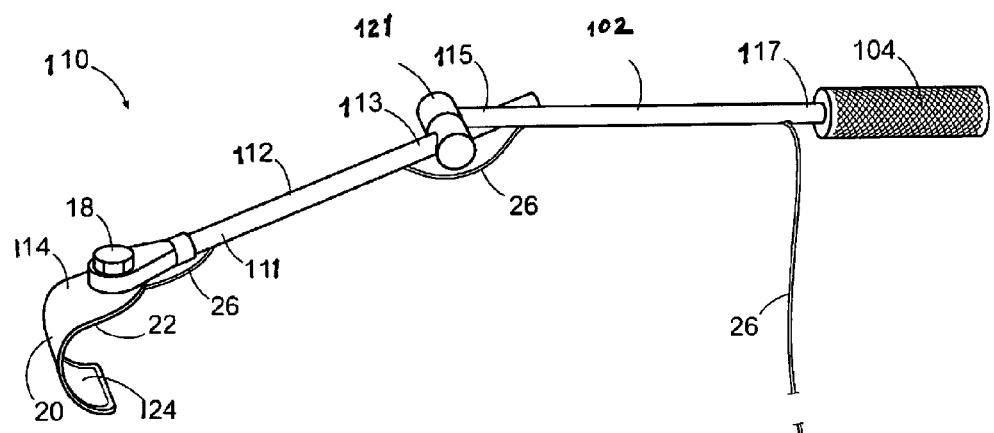
FIG. 5 illustrates another embodiment of a Doppler retractor of the present invention.
Figure 5:
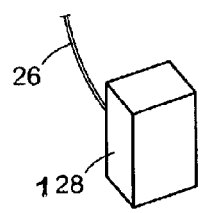

FIG. 5 illustrates another embodiment of Doppler retractor 10 of the present invention. In FIG. 5, Doppler retractor 110 comprises arm 112 having first end 111 and second end 1 13. Blade 114 is fixed to arm 112 at one of first end 111 and second end 113. It is preferable that blade 114 is attached to arm 112 in a movable manner. Extension arm 102 is fixed to one of first end 111 and second end 113 of arm 112 such that extension arm 102 opposes blade 114. It is preferable that extension arm 102 may be movably attached to arm 112 with attachment dial 121 to allow for tow-in and tow-out adjustment. Dial 121 may be a tension-type dial, a ratchet-type dial, a screw-type dial, or any other movable connector to adjust the physical relation of extension arm 102 and arm 112.

Extension arm 102 may be substantially elongated and defined by first end 115 and second end 117. Extension arm 102 may be fixed to arm 112 at one of first end 115 and second end 117 of extension arm 102. Extension arm 102 may be also be movably fixed to arm 112 at one of first end 115 and second end 117 of extension arm 102. Handle 104 is fixed to one of first end 115 and second end 117 such that handle 104 opposes arm 112.

Blade 114 preferably includes outer surface 120 and contact surface 122. In use, contact surface 122 of blade 114 is in contact with the patient 204 to a point adjacent to surgical site 210 (as shown in FIG. 1). Blade 114 further includes transducer 124 disposed on the contact surface 122. Wire 126 extends from transducer 124 to Doppler ultrasound sensor 128 to provide electronic communication between transducer 124 and Doppler ultrasound sensor 128.

Arm 112 of Doppler retractor 110 illustrated in FIG. 5 may comprise an aperture (as illustrated in FIG. 3) through which wire 126 can be received. In the alternative, arm 112 of Doppler retractor 110 illustrated in FIG. 5 may comprise clips 32 (as illustrated in FIG. 4), which grip wire 126 in order to maintain wire 126 substantially adjacent to arm 112.

Extension arm 102 of Doppler retractor 110 illustrated in FIG. 5 may comprise an aperture (as illustrated in FIG. 3) through which wire 126 can be received. In the alternative, arm 112 of Doppler retractor 110 illustrated in FIG. 5 may comprise clips 32 (as illustrated in FIG. 4), which grip wire 126 in order to maintain wire 126 substantially adjacent to extension arm 102.

It should be emphasized that the above-described embodiments of the present invention are possible examples of implementations, set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A surgical retractor, comprising:
   a retractor frame having first and second support bars spaced from each other to define a surgical site:
   a first arm having a first end and a second end, said first end being operative to movably attach to said first bar support;
   a first blade having an outer surface and a contact surface and being attached to said second end of said first arm;
   a transducer disposed on said contact surface of said first blade;
   a second arm having a first end and a second end, said first end of said second arm being operative to movably attach to said second bar support;
   a second blade having an outer surface and a contact surface and being attached to said second end of said second arm; and
   a Doppler ultrasound sensor in electrical communication with said transducer and operative to indicate when a preset blood flow rate is detected;
   wherein said transducer is operative to transmit signals to said Doppler ultrasound sensor such that said sensor calculates a blood flow rate proximate to a surgical site where the surgical retractor is being used.

2. The surgical retractor of claim 1, further comprising:
   a retractor frame support arm;
   wherein said retractor frame support arm is arranged and configured to be attached to and to support the first and second bar.

3. The surgical retractor of claim 1, wherein said Doppler ultrasound sensor comprises a visual indicator adapted to indicate when the preset blood flow rate is detected.

4. The surgical retractor of claim 1, wherein said Doppler ultrasound sensor comprises an audible indicator adapted to indicate when the preset blood flow rate is detected.

5. The surgical retractor of claim 1, wherein said Doppler ultrasound sensor comprises an audible sensor adapted to indicate blood flow.

6. The surgical retractor of claim 1, wherein said transducer comprises piezoelectric crystals.

7. The surgical retractor of claim 1, further comprises:
wire extending from said transducer to said Doppler ultrasound sensor and providing communication between said transducer and said Doppler ultrasound sensor.

8. The surgical retractor of claim 7, further comprising:
a clip arranged and configured to hold said wire substantially adjacent to said first arm.

9. The surgical retractor of claim 7, wherein said first arm has an aperture arranged and configured to receive said wire therethrough.

10. The surgical retractor of claim 7, wherein said first arm is substantially hollow and arranged and configured to receive said wire therein.

11. The surgical retractor of claim 7, wherein said first blade is curved.

12. A surgical retractor, comprising:
a retractor frame having an elongate support bar;
an arm having a first end and a second end and being operative to movably attach to the support bar;
an extension arm having a first end and a second end, said first end of said extension arm being attached to said second end of said arm;
a handle located adjacent to said second end of said extension arm such that said handle opposes said arm;
a blade having an outer surface and a contact surface and being attached to said first end of said arm such that said blade opposes said extension arm;
a transducer disposed upon said contact surface of said blade; and
a Doppler ultrasound sensor in electrical communication with said transducer and operative to indicate when a preset blood flow rate is detected;
wherein said transducer is operative to transmit signals to said Doppler ultrasound sensor such that said sensor calculates blood flow rate proximate to a surgical site where the surgical retractor is being used.

13. The surgical retractor of claim 12, wherein said Doppler ultrasound sensor comprises a visual indicator adapted to indicate when the preset blood flow rate is detected.

14. The surgical retractor of claim 12, wherein said Doppler ultrasound sensor comprises an audible indicator adapted to indicate when the preset blood flow rate is detected.

15. The surgical retractor of claim 12, wherein said Doppler ultrasound sensor comprises means for indicating when the preset blood flow rate is detected.

16. The surgical retractor of claim 12, wherein said Doppler ultrasound sensor comprises an audible sensor adapted to indicate blood flow.

17. The surgical retractor of claim 12, wherein said transducer comprises piezoelectric crystals.

* * * * *